United States Patent [19]

Oyama et al.

[11] Patent Number: 4,563,263
[45] Date of Patent: Jan. 7, 1986

[54] SELECTIVELY PERMEABLE FILM AND ION SENSOR

[75] Inventors: Noboru Oyama, Higashikurume; Hiroaki Matsuda, Musashino; Eishun Tsuchida, Sekimachi; Yukio Ohnuki, Suifu; Takeshi Shimomura, Kawasaki; Norihiko Ushizawa, Honmachi, all of Japan

[73] Assignee: Terumo Corporation, Tokyo, Japan

[21] Appl. No.: 339,715

[22] Filed: Jan. 15, 1982

[51] Int. Cl.⁴ ............................................. G01N 27/26
[52] U.S. Cl. .................................. 204/418; 204/433; 204/1 T
[58] Field of Search .............. 204/195 M, 1 H, 290 R, 204/56 R, 416, 433, 434, 418, 415; 428/458, 457

[56] References Cited

U.S. PATENT DOCUMENTS

| | | | |
|---|---|---|---|
| 3,840,452 | 10/1974 | Baum et al. | 204/418 |
| 4,115,209 | 9/1978 | Freiser et al. | 204/195 M |
| 4,151,049 | 4/1979 | Janata | 204/195 M |
| 4,334,054 | 6/1982 | Dubois et al. | 428/457 |

FOREIGN PATENT DOCUMENTS

| | | |
|---|---|---|
| 0021626 | 1/1981 | European Pat. Off. |
| 1515025 | 6/1978 | United Kingdom |
| 2030358 | 4/1980 | United Kingdom |

OTHER PUBLICATIONS

LeBlanc, O. H., Grubb, W. T., "Long-Lived Potassium Low Selective Polymer Membrane Electrode", Anal Chem., vol. 48, No. 12, pp. 1658–1660, 10/76.

Primary Examiner—John F. Niebling
Assistant Examiner—B. J. Boggs, Jr.
Attorney, Agent, or Firm—Frishauf, Holtz, Goodman & Woodward

[57] ABSTRACT

A selectively permeable film directly applied to coat the surface of an electroconductive element, said electively permeable film comprising a polymer which is derived from at least one aromatic compound selected from the group of nitrogen-containing aromatic compounds or from the group of hydroxy aromatic compounds. The nitrogen-containing aromatic compounds are aniline, 2-aminobenzotrifluoride, 2-aminopyridine, 2,3-diaminopyridine, 4,4'-diaminodiphenyl ether, 4,4'-methylenedianiline, tyramine, N-(o-hydroxybenzyl)-aniline and pyrrole. The film coated on the electrode surfaces permits selective passage of ions and the electrode can be used as an ions sensor for measuring the concentration of ions in solutions.

8 Claims, 9 Drawing Figures

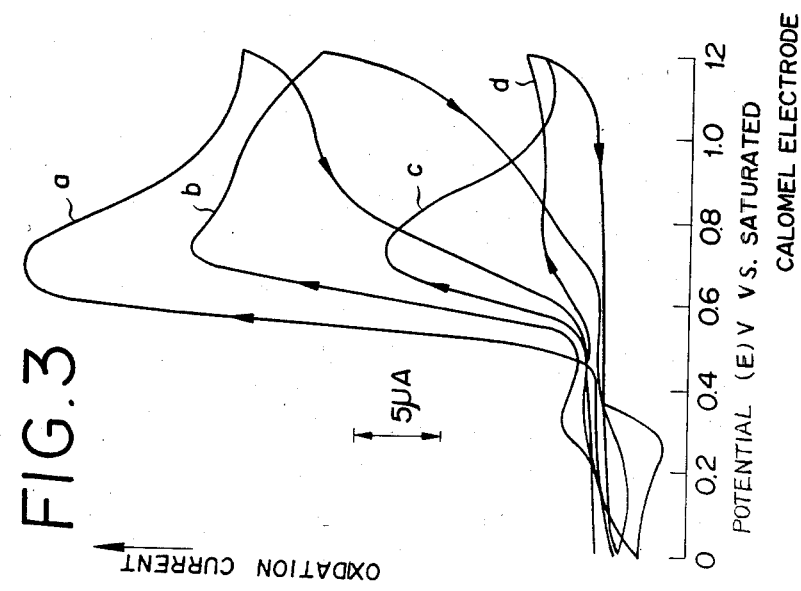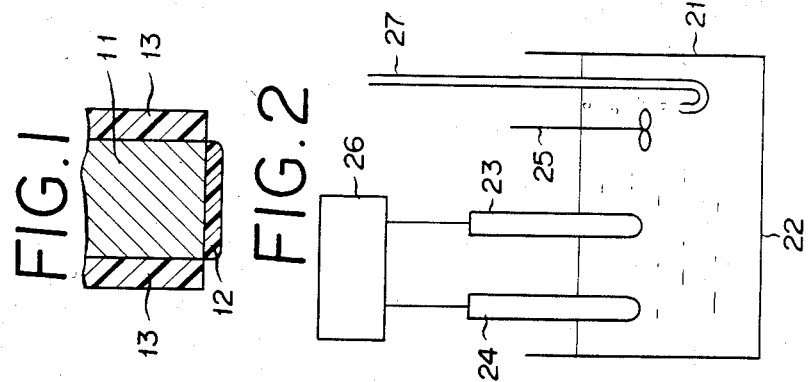

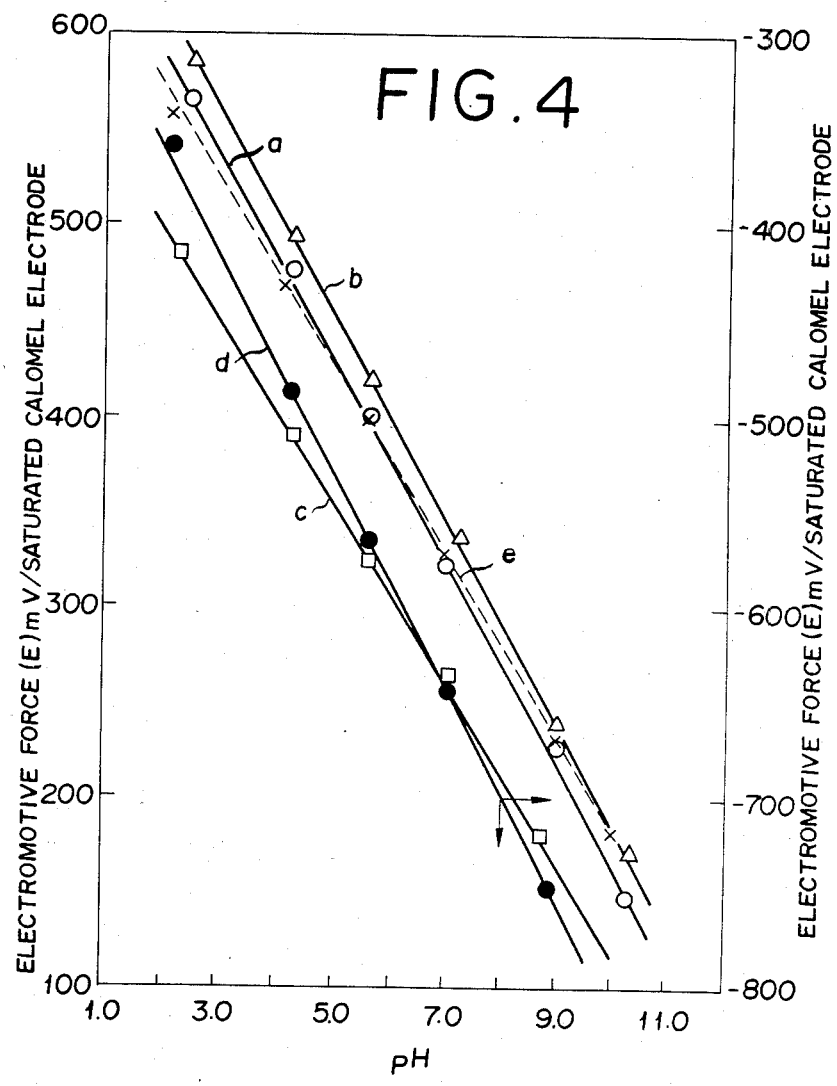

SELECTIVELY PERMEABLE FILM AND ION SENSOR

BACKGROUND OF THE INVENTION

1. Field of the Invention

This invention relates to a selectively permeable film and an ion sensor. More particularly, this invention relates to a selectively permeable film having a polymer film suitable for use such as an ion sensor applied directly in the form of a coat to the surface of an electroconductive substrate and to an ion sensor using such a selectively permeable film. Particularly, the ion sensor contemplated by this invention is of a type having a polymer film applied directly in the form of a coat to the surface of an electroconductive substrate and serving the purpose of permitting the measurement of an ion concentration in a given solution by means of electrode potential or current response.

2. Description of Prior Arts

Recently, the coating on the surface of an electroconductive material with a film for the purpose of conferring various functions upon the electroconductive material has been gaining in popularity. Generally, an electrode coated with such a film is called a polymer coated electrode. The coated electrode is expected to serve as an electrode capable of manifesting a novel function suitable for use in catalysts, transducers and sensors. For the exploitation of the function, due consideration should be paid to the quality of the electroconductivity and ion-selectivity of the film applied directly in the form of a coat to the surface of the electroconductive substrate. The electrodes of the class such as are used in the form of ion sensors and pH sensors, for example, are required to possess selectivity and permeability with respect to the kinds of ions subjected to detection. No film material which possesses the selective permeability and, at the same time, functions advantageously as a coat for the electrode, however, has so far been found.

Heretofore, the hydrogen electrode and the quinhydrone electrode have been known as electrodes available for measuring the concentration of a hydrogen ion in a solution. Nowadays, because of simplicity of usage and improved accuracy of measurement, the glass electrode has come to find increasing acceptance. The principle which underlies the measurement of the pH value of a given solution by the glass electrode is that when the given solution of an unknown hydrogen ion concentration and the reference solution of a constant hydrogen ion concentration are opposed to each other across a thin glass membrane, the potential difference between the two solutions appears on the opposite surfaces of the thin glass membrane and the measurement of this potential difference permits determination of the pH value.

The glass electrode, therefore, is required to possess an area for holding the reference solution and does not permit easy reduction of size. When the given solution happens to contain a viscous substance, the viscous substance adheres to the surface of the thin glass membrane rendering the measurement of the pH value difficult or impairing the reproducibility of the electrode potential response. Further, since the resistance offered by the glass membrane of the glass electrode is so large as to range from 10 to 100 MΩ, the ordinary potentiometer cannot be used by itself but must be used in combination with an amplifier of high-input impedance for effective measurement of the pH value.

An object of this invention, therefore, is to provide a selectively permeable film which is capable of being directly coated on the surface of an electroconductive substrate and, at the same time, is possessed of ion-selective permeability.

Another object of this invention is to provide an ion sensor which obviates the necessity for providing an area for holding the reference solution and permits desired reduction in size.

SUMMARY OF THE INVENTION

These objects are accomplished by a selectively permeable film of a form directly coated on the surface of an electroconductive substrate. The permeable film comprises polymers derived from at least one aromatic compound selected from the group consisting of nitrogen-containing compounds selected from the group consisting of aniline, 2-aminobenzo-trifluoride, 2-aminopyridine, 2,3-diaminopyridine, 4,4'-diaminodiphenyl ether, 4,4'-methylenedianiline, tyramine, N-(o-hydroxybenzyl)aniline and pyrrole and the group of hydroxy aromatic compounds, which permit selective passage of ions.

The objects of the invention are also accomplished by an ion sensor for measuring the concentration of an ion in a given solution by electrode potential response or current response. The ion sensor is prepared by coating the surface of an electroconductive substrate with a polymer film derived from at least one aromatic compound selected from the group consisting of nitrogen-containing aromatic compounds and hydroxy aromatic compounds mentioned above. The present invention makes use of the heretofore hardly practiced technique of chemically modifying the surface of an electroconductive material with a polymer. By this technique of chemical modification, the electrode surface acquires selective permeability to dissolved ions, enjoys protection of its own surface against otherwise possible corrosion or dissolution, and produces the entirely novel function of responding to the concentration of ions in the solution with the variation of the electrode potential or current. The electrode of this invention is quite unlike the working mechanism of the glass electrode.

The polymer coated electrode mentioned above possesses a low impedance. This polymer film may be either an electrolytically oxidized polymer film polymerized on the surface of an electroconductive element by means of electrochemical oxidation or a polymer film obtained by dissolving the polymer in a solvent, applying the resultant solution to the surface of an electroconductive element and drying the wet polymer layer formed thereon. From the standpoint of performance, the polymer film produced by the former method is more desirable. The ion sensor incorporating a polymer film derived from a nitrogen-containing aromatic compound and hydroxy aromatic compounds is advantageously used as a pH sensor.

The term "polymer" as used in the present specification shall embrace both homopolymers and interpolymers (such as, for example, copolymers and terpolymers).

BRIEF DESCRIPTION OF THE DRAWINGS

FIG. 1 is an enlarged cross section of part of the ion sensor according to the present invention.

FIG. 2 is a schematic diagram illustrating a method for measuring the pH value of a given solution by the ion sensor of the present invention.

FIG. 3 is a cyclic voltammogram obtained during the electrochemical oxidation of 4,4'-diaminodiphenyl ether.

FIG. 4 is a graph showing the relation between the electromotive force of the polymer coated electrode and the pH value under bubbling the gas into the test solution.

PREFERRED EMBODIMENT OF THE INVENTION

Figure 5:
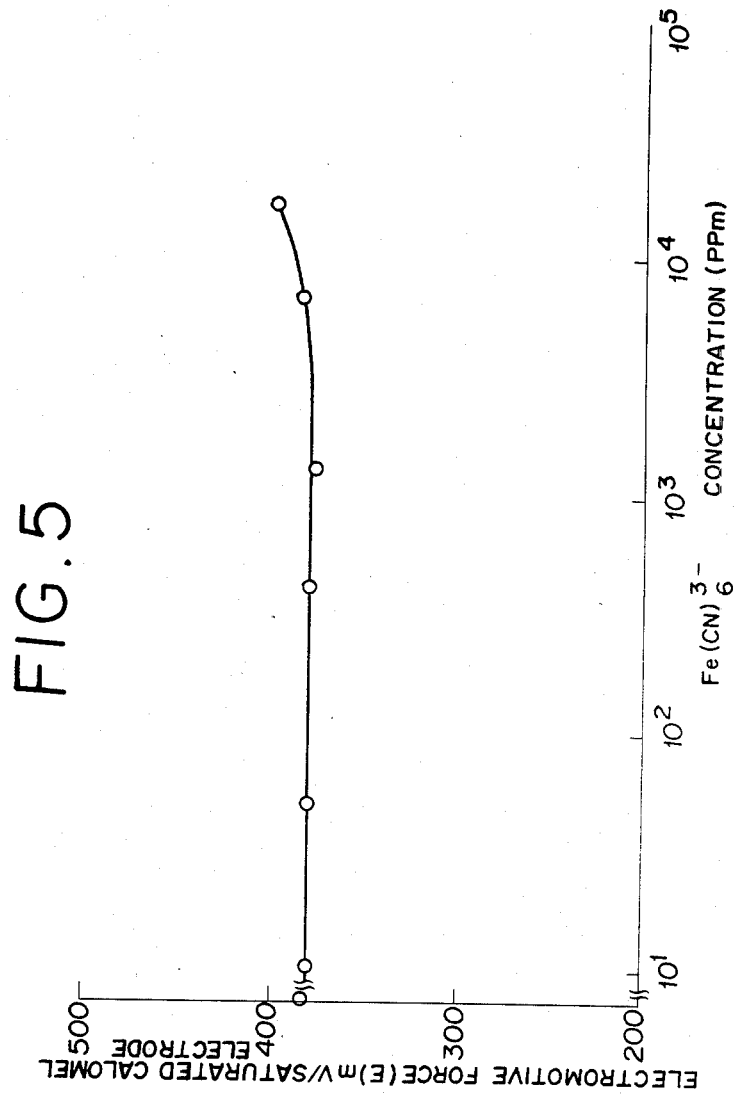
FIG. 5 is a graph showing the dependence of the equilibrium potential upon the ferricyanide concentration dissolved in the test solution.

The present invention will be described in detail below with reference to the accompanying drawing.

As illustrated in FIG. 1, the ion sensor of this invention comprises an electroconductive element 11 of any desired shape such as a bar, an insulation 13 of polyolefin or Teflon applied to coat the peripheral surface of the electroconductive element, and a prescribed polymer film 12 directly coated on the exposed disk surface of the electroconductive element. The electroconductive element 11 is made of an electroconductive material, preferably platinum.

The polymer film 12 which is directly coated on the disk surface of the electroconductive element 11 is made of a polymer of nitrogen-containing aromatic compounds. The nitrogen-containing aromatic compound is at least one reagent selected from the group consisting of aniline, 2-aminobenzotrifluoride, 2-aminopyridine, 2,3-diaminopyridine, 4,4'-diaminodiphenyl ether, 4,4'-methylenedianiline, tyramine, N-(o-hydroxybenzyl)aniline and pyrrole. Presynthesized polymers include aromatic polyamides and/or imides. One concrete example is a polyamide polymer obtained by reacting a polyamide-imide compound of 4,4'-diaminodiphenyl ether or 4,4'-diaminodiphenyl methane derivative and bis-cyclo-(2,2,2)-oct-7-ene-2,3,5,6-tetracarboxylic dianhydride with thionyl chloride to yield an acid chloride, and subsequently reacting the acid chloride with 4,4'-diaminophenyl ether [see Kobayashi et al: Journal of Japan Chemical Society, (12) 1929-1932 (1980)]

The polymer film 12 can also be prepared from a derivative of hydroxy aromatic compounds. One such hydroxy aromatic compound can be represented by the general formula:

(wherein, Ar denotes an aromatic ring, each R denotes a substituent, and l denotes zero or the valency number of Ar). The aromatic ring, Ar, can be a monocyclic ring (such as, for example, a benzene ring or pyridine ring) or a polycyclic ring (such as, for example, a quinoline ring, naphthoquinone ring, or bisphenol ring). Examples of the substituent R includes alkyl groups such as methyl group, halogenated alkyl groups, aryl groups such as phenyl group, alkylcarbonyl groups and arylcarbonyl groups

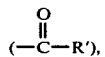

hydroxy-alkyl group (—R''OH), carboxyl groups, aldehyde groups and hydroxyl groups.

Concrete examples of these hydroxy aromatic compounds are phenol, dimethyl phenols (such as, for example, 2,6- and 3,5-dimethyl phenols), 2-, 3- and 4-hydroxypyridines, o- and m-benzyl alcohols, o-, m- and p-hydroxybenzaldehydes, o-, m- and p-hydroxyacetophenones, o-, m- and p-hydroxypropiophenones, o-, m- and p-benzophenols, o-, m- and p-hydroxybenzophenones, o-, m- and p-carboxyphenols, diphenyl phenols (such as, for example, 2,6- and 3,5-diphenylphenols), 2-methyl-8-hydroquinone, 5-hydroxy-1,4-naphthoquinone, 4-(p-hydroxyphenyl)-2-butanone, 1,5-dihydroxy-1,2,3,4-tetrahydronaphthalene and bis-phenol A. Examples of presynthesized polymers are polyphenylene oxide, polyphenylene oxide derivatives, polydiphenylphenylene oxide, polydimethylphenylene oxide and polycarbonate.

The direct coating of the polymer film of the aforementioned nitrogen-containing aromatic compound or hydroxy aromatic compound on the disk surface of the electroconductive element 11 can be accomplished by a method which involves polymerizing the nitrogen-containing aromatic compound or hydroxy aromatic compound to be polymerized on the surface of the electroconductive element 11 by the technique of electrochemical oxidation polymerization, a method which involves dissolving the synthesized polymer in a solvent, spreading the resultant solution on the disk surface and drying the wet layer or a method which involves directly fastening the polymer film to the surface of the electroconductive material by a chemical or physical treatment or by irradiation.

Of the aforementioned methods available for the coating, the most advantageous is the method of electrochemical oxidation polymerization. A suitable solvent and a supporting electrolyte are chosen for the reaction of the electrochemical oxidation polymerization.

For example, the electrochemical oxidation polymerization of 2-aminobenzotrifluoride or 4,4'-diaminodiphenyl methane is carried out in a phosphate, buffer of pH 7, that of aniline in an acetonitrile solution containing pyridine and sodium perchlorate that of 4,4'-diaminodiphenyl ether in either an acetonitrile solution containing sodium perchlorate or a methanol solution containing sodium hydroxide, and that of pyrrole in an acetonitrile solution containing tetrabutylammonium hexafluorophosphate [Bu$_4$N(FF$_6$)] as a supporting electrolyte. The electrochemical oxidation polymerization of a hydroxy aromatic compound is carried out in a solvent such as alkaline methanol.

The polymer film which has been prepared by the electrochemical oxidation polymerization possesses extremely stable adhesion and a very smooth surface. Although the thickness of the polymer film is not specifically limited, it is desirable that it be in the range of 0.01 to 1 μm.

The functions exploited by the coated electrode of the aforementioned construction will be described in detail below.

(1) Response as an ion sensor

For the measurement of the pH value of a given test solution with the ion sensor of FIG. 1, the test solution 22 subjected to pH measurement is placed in a vessel 21 and then the ion sensor 23 of this invention and a reference electrode 24 such as a silver-silver chloride electrode or saturated calomel electrode are immersed in the test solution. Then, the potential difference (electromotive force) of the ion sensor 23 relative to the reference electrode 24 is measured with a potentiometer 26. In this case, it is desirable that the test solution 22 is desired to be stirred with a stirrer 25. The pH value of the test solution is read out of the graph prepared in advance to show the relation between the electromotive force and the pH value. To blow a gas into the solution, a blow pipe 27 is available.

The relation between the electromotive force and the pH value obtained with the ion sensor of this invention shows a linear relation of an inclination of 59 mV/pH in a wide range of pH values, satisfying the Nernst equation shown below.

$$E = E_o + (RT/F)\ln[H^+]$$

(wherein, E denotes the electromotive force (mV), $E_o$ the constant potential (mV), R the gas constant T the absolute temperature, F the Faraday constant and $[H^+]$ the hydrogen ion concentration). During the measurement, the test solution is held in an open system or under the flow of oxygen gas introduced through the blow pipe 27. When the measurement of the electromotive force is carried out under the flow of hydrogen gas, the measured value is heavily shifted to a minus value. Nevertheless, the value satisfies the Nernst equation with reference to the hydrogen ion.

(2) Selective permeation of ion through film and its control

The aforementioned polymer film which is directly coated on the electrode shows selective permeability to the ions in the solution. For a rigorous hydrodynamic treatment of the selective permeability, the hydrodynamic voltammometry method using a rotating disk electrode (RDE) is available. The amount of mass transfer of ions to the electrode can be controlled by suitably changing the rotation rate of the disk electrode. The selective permeability of the film to a given chemical species, therefore, can be evaluated by comparing the electrode coated with the polymer film and the bare electrode with respect to the dependency of the limiting current of the voltammogram upon the rotation rate. Although this behavior varies with the kind of the polymer film coating the electrode and the kind of dissolved ions, the permeation of ions is proportionally impeded as the thickness of the polymer film increases and the permeation of ions through the film is proportionally curbed as the volume of dissolved ions increases.

To cite other functions, the polymer film directly coated on the surface of the electrode permits improvement in the quality of the electrode surface and possibly contributes to enhancing the catalytic activity of the electrode and preventing the surface of the electrode from otherwise possible corrosion or dissolution. Further, the coated polymer film has the ability to be an anchor for the introduction of a suitable substituent to the surface of the electroconductive element. When the surface of the electrode is destitute of a suitable substituent which is effective in converting the surface into a compound through reaction with an organic substance, the surface of the electrode is first coated with a polymer having a substituent such as aldehyde or amine. Then the polymer film formed thereon can be utilized as a reactive substituent for the graft polymerization reaction and also as a binding substrate for the desired compound. When the substituent of the coated polymer film is a ligand such as pyridine, the polymer film possesses an ability to form a coordination bond. When the substituent is sulfonic acid or quaternized pyridine which possesses a charge, the coated film possesses the nature of a poly-electrolyte and the ability to collect and fix oppositely charged ions. Consequently, the electrode which is directly coated with the polymer film described above possesses ability to pre-concentrate a minute amount of dissolved ions, then detects these ions with the current in consequence of oxidation or reduction performed on the electrode, and possibly functions as a sensor for the detection of trace ions. The coated polymer film which forms an insulation can be converted into an electroconductive film by introduction of suitable compounds within the polymer film. Further, the state of oxidation or reduction of the redox center in the film can be altered by suitably changing the potential of the electrode, making it possible to change the color of the film or to color or decolor the film.

The present invention is described below with reference to working examples. The rotating disc electrode (RDE) of platinum to be mentioned in the following examples has an area of $4.4 \times 10^{-3}$ cm$^2$.

EXAMPLE 1

A platinum wire as an electroconductive element had its periphery coated with tetrafluoroethylene resin (made by E. I. DuPont De Nemours & Co., Inc., and marketed under the trademark designation "Teflon") as an insulation and its disk electrode surface was subjected to the following treatments for the purpose of conditioning the surface before electrolysis. First, the disk surfaces were polished with silicon carbide paper and alumina powder (0.3 μm), washed with dilute aqua regia, cleaned with distilled water, and immersed in a 0.05M acetic acid solution to afford an electrode. The electrode was set up in an ordinary H-type cell together with a platinum net used as an counter electrode and a sodium chloride-saturated calomel electrode (SSCE) used as a reference electrode. The voltage applied to the electrodes was swept alternately between $-0.6$ V and $+1.0$ V vs. SSCE about ten cycles to activate the surface of the electrode. The activated electrode was washed with distilled water, washed with methanol, and dried.

The preparation of an electrode coated with a polymer film was carried out by immersing the pretreated platinum wire in an acetonitrile solution (electrolytic solution) containing a 10 mM 4,4'-diaminodiphenyl ether and 0.1M sodium perchlorate. The electrolytic solution was thoroughly deoxygenated with argon gas before electrolysis. After the occurrence of the oxidation polymerization reaction of the 4,4'-diaminodiphenyl ether monomer on the platinum electrode was confirmed, the applied voltage was set at $+1.20$ volts vs. SSCE to perform electrolysis for 10 minutes and the coating of the electrode surface was carried out. Then, the electrode surface was washed with distilled water at least three times to finish the desired electrode coated with the electrochemical oxidation polymer film. FIG. 3 represents a cyclic voltammogram showing the beginning of the electrolytic oxidation polymerization. The difference in peak current between the first scanning oxidation wave (curve "a") and the second scanning oxidation wave (curve "b") is ascribable to the formation of the coating film on the electrode surface. The curve "c" and "d" are the third and fourth scanning waves. The scan rate of the potential sweep was 74 mV/second.

The polymer-coated electrode produced as described above was tested for performance as a pH sensor. As the solution for the pH measurement, a buffer solution having a total phosphoric acid content of 50 mM was used. The pH value of the buffer solution was changed in the range from 2.00 to 10.00 with sodium hydroxide and perchloric acid. The polymer-coated electrode was immersed in the test solution and the electromotive forces vs. SSCE were measured. Plots of the value of electromotive forces obtained with the measurement and the pH value measured by a commercially available glass electrode were satisfied with a straight line "a" in the graph of FIG. 4. The slope of the straight line which is 54 mV/pH corresponds to a value substantially satisfying the Nernst equation in the pH range of 2.0 to 11.0. The measurement was carried out in an open system in which the test solution was left standing in the ambient air. When the measurement was made while oxygen gas or argon gas was passed into the test solution, responses represented by the straight lines "b" and "c", respectively, were obtained, as shown in FIG. 4. The slopes of these straight lines were 54 mV/pH and 46 mV/pH respectively. Under the flow of hydrogen gas, the relation (straight line "d") still satisfied the Nernst equation with the slope of 59 mV/pH, although the value of the electromotive force was heavily shifted to the minus side in the pH range of 2.0 to 9.0.

The results indicate that the electrode coated with the polymer film possessed an excellent property for the determination of hydrogen ion concentration. The accuracy and stability of the equilibrium electrode potential (electromotive force) response were high. The potential reached a constant within 5 to 15 minutes. For several hours thereafter, the potential remained at the constant level accurately within +2 mV. When this electrode was immersed in a phosphate buffer solution at pH 7.0 for one week and then tested for electromotive force response relative to hydrogen ion, the results of the test gave the straight line "e" of FIG. 4, which satisfies the Nernstian. This fact attests to the outstanding durability of the film. A similar measurement was carried out in the test solution additionally containing cobalt (II) ion, nickel (II) ion, iron (II) ion or zinc (II) ion. The equilibrium potential was not influenced by these ions. The results of the test which was performed in the solution containing ferricyanide (pH=4.0) are shown in FIG. 5. The equilibrium potential was also not influenced, when the test solution contained alkaline earth metal ions such as calcium (II) ion.

EXAMPLE 2

Coating of the surface of a platinum electrode by the electrochemical oxidation polymerization of aniline was carried out in an acetonitrile solvent containing 10 mM aniline, 20 mM pyridine and 0.1M sodium perchlorate. The polymer coating of the electrode was produced by following the procedure of Example 1, i.e. by the technique of electrochemical oxidation polymerization. When the prepared polymer coated electrode was tested for response as a pH sensor, a linear relation having a slope of 52 mV/pH in the pH range of 2.0 to 9.0 was obtained. The electrode potential reached a constant value within 5 to 10 minutes. For several hours thereafter, the value remained stable within +2 mV. Although the coated polymer film showed extremely high durability, the equilibrium potential was influenced by the concentration of transition metal ions contained in the test solution.

EXAMPLE 3

Electrochemical oxidation polymerization on the surface of a platinum electrode was carried out in an acetonitrile solution containing 10 mM of pyrrole and 50 mM of $Bu_4N(PF_6)$ as a supporting electrolyte. Consequently, a polymer coated electrode similar to Example 1 was obtained. In this case, the electrochemical oxidation polymerization of pyrrole was carried out at a constant potential kept at +0.8 volt vs. SSCE for 10 minutes. The electrode thus treated was washed with water and methanol and then dried. The polymer film thus produced assumed a purple color. When the coated electrode was tested for response as a sensor, a linear relation of a slope of 48 mV/pH in the pH range of 2.0 to 9.0 was obtained. The electrode potential reached a constant value within 5 to 30 minutes. For several hours thereafter, the value remained stable within ±2 mV. When the test was carried out while oxygen or argon gas was passed into the test solution, the linear relations having slopes of 57 mV/pH ($2.0 \leq pH \leq 10$) and 48 mV/pH ($2.0 \leq pH \leq 9.0$) were respectively obtained. The potential reached a constant value within 20 to 40 minutes. For several hours thereafter, the value kept constant within ±2 mV. The same results were also obtained when this electrode was immersed in a phosphate buffer solution (at pH=7.0) for five days and subsequently used for measuring the hydrogen ion concentration. This fact attests to the outstanding durability of the polymer coating. The equilibrium potential was little influenced when transition metal ions were contained in the test solution.

EXAMPLE 4

The coating polymer film of 2-aminopyridine on a platinum electrode surface was carried out by the same technique of electrochemical oxidation polymerization as used in Example 1, in a 50 mM phosphate buffer solution containing 10 mM of 2-aminopyridine (pH=7.0). A linear relation was established between the equilibrium potentials of the polymer-coated electrode and the pH values. The linear relation had a slope of 48 mV/pH in the pH range of 2.0 to 11.0. In this case, the test was performed in an open system where the test solution was exposed to air. When the test was conducted while oxygen or argon gas was passed into the test solution, linear relations having slopes of 48 mV/pH and 59 mV/pH (in the respective pH ranges of 2.00 to 11.00 and 2.00 to 10.5) were obtained. When hydrogen gas was passed into the test solution, the values of electromotive forces were heavily shifted to the minus side. Nevertheless, the linear relation satisfied the Nernst equation with the slope of 59 mV/pH.

The equilibrium potential reached a constant value within 5 to 20 minutes. For several hours thereafter, the value kept constant within ±2 mV. The same pH response was obtained when the electrode was immersed in a phosphate buffer solution of pH 7.0 for 10 days and subsequently tested for electromotive force response to hydrogen ion. This fact attests to the extremely high durability of the membrane of this invention.

EXAMPLES 5 AND 6

By following the procedure of Example 1, polymer film-coated electrodes of 2,3-diaminopyridine and 2-aminobenzo-trifluoride were prepared. The equilibrium potential response and the influence of the gas passing (oxygen, argon and hydrogen) for these electrodes were tested on the measurement of hydrogen ion concentration in the test solution. The results are shown in Table 1 below.

TABLE 1

| Example | Monomer | System | Relation of mV/pH found from slope of straight line | pH range where a linear relation is satisfied | Time required to attain an equilibrium potential (minute) |
|---|---|---|---|---|---|
| 5 | 2,3-Diaminopyridine | Open | 54 | 3.5–11.0 | ~20 |
| | | Passing of oxygen | 54 | 3.5–11.0 | 10~40 |
| | | passing of hydrogen | 58 | 2.0–8.0 | ~10 |
| 6 | 2-Aminobenzo-trifluoride | Open | 48 | 2.0–9.0 | 10~60 |
| | | passing of oxygen | 47 | 2.0–9.0 | ~25 |
| | | passing of hydrogen | — | No linear relation obtained | No equilibrium (potential obtained in more than 2 hours) |

EXAMPLE 7

Figure 6:
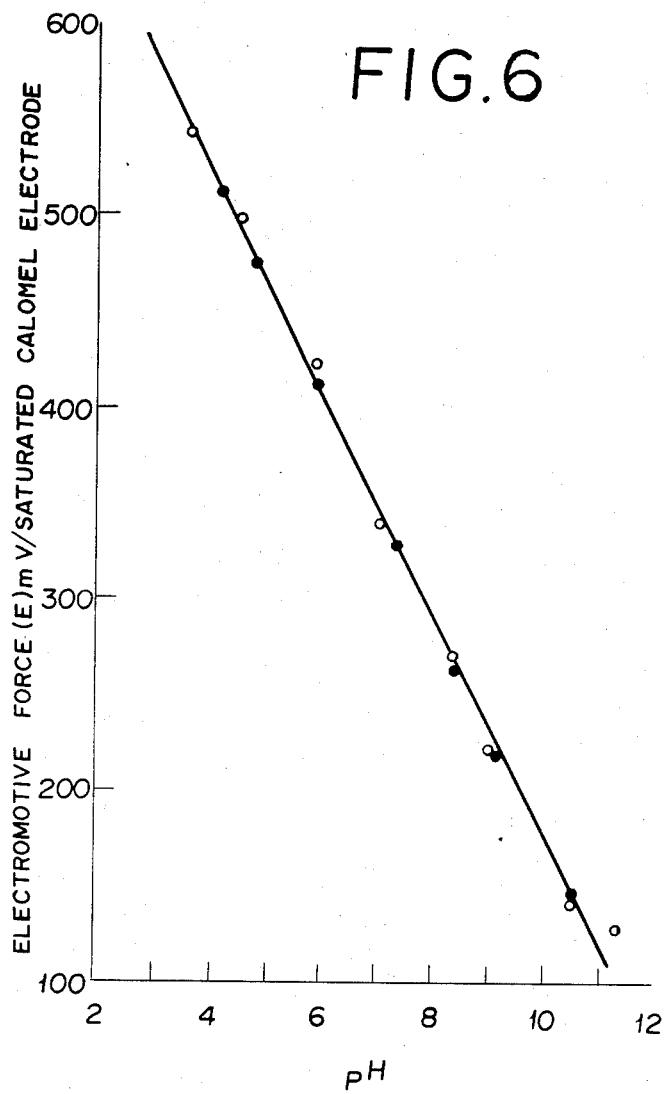
FIG. 6 is a graph showing the relation between the electromotive force of the electrode coated with poly(phenylene oxide) and the pH value.

The coating of polymer film of phenol on a platinum electrode surface was carried out by the same technique of electrochemical oxidation polymerization as used in Example 1. The electrolytic solution was methanol solvent containing 10 mM phenol and 30 mM of sodium hydroxide. It was thoroughly deoxygenated with argon gas. By the scanning of applied voltage, the occurrence of the oxidation reaction of phenol monomer on the surface of the platinum electrode was confirmed. Then, the applied voltage was set to 0.9 volt vs. SSCE and the electrolysis was continued for three minutes to coat the surface of the electrode with the product of the oxidation polymerization. Then, the surface of the electrode was washed with distilled water at least three times. The film-coated electrode was immersed in a given test solution and its electromotive force versus a silver-silver chloride electrode (Ag-AgCl electrode) used as the reference electrode was measured. Plotting the electromotive forces of the coated electrode relative to the pH values measured with a commercially available gas electrode is indicated by blank circles in the graph of FIG. 6. The straight line thus obtained had the slope of 59 mV/pH in a wide pH range and satisfied the Nernst equation completely. AC impedance measurement of the pH sensor prepared was carried out. The results are shown in Table 2. The changes in the components of resistance and the component of capacitance before and after the coating of the polymer film were small, indicating that a pH sensor of extremely low impedance was provided. This test was carried out in a 0.05M phosphate buffer solution of pH 7 by using a platinum disk as an electrode.

TABLE 2

| Results for AC impedance measurement (frequency 1 kHz) | | |
|---|---|---|
| Use of film on the surface of platinum electrode | Resistance ($\Omega/cm^2$) | Capacitance ($\mu F/cm^2$) |
| No | 444 | 0.19 |
| Yes | 450 | 0.20 |

At the applied voltage, −0.2 V vs. SSCE.

Concerning the accuracy and stability of the electrode potential (electromotive force) response, the potential reached a constant value within 3 to 5 minutes. For several hours thereafter, the value kept constant within ±2 mV. These results indicate that the electrode was highly ideal for the measurement of hydrogen ion concentration. The Nernst equation was satisfied in the pH range from 3.0 to 10.5. This means that the electrode of this invention had the same pH range for effective measurement as the glass electrode.

Then, the electrode was immersed in a phosphate buffer solution of pH 7 for 24 hours and thereafter the electromotive forces of the electrode were measured. The result is indicated by solid circles in the graph of FIG. 6. Also in this case, the straight line satisfied the Nernst equation, indicating that the coated electrode had outstanding durability. The equilibrium potential was influenced by the concentration of transition metal ions contained in a test solution.

EXAMPLES 8 THROUGH 27

By following the procedure of Example 7, various hydroxy aromatic compounds were polymerized on a platinum electrode to coat on the electrode surface. The function as a pH sensor was examined with the prepared electrodes. The results are summarized in Table 3. It is noted that the electrodes with polymer coating prepared by electrochemical oxidation of o-hydroxybenzophenone and 3,5-dimethylphenol among them functioned excellently as sensors for the measurement of hydrogen ion concentration.

TABLE 3

Nernstian response of electrode coated with polymer films of hydroxy aromatic compounds Platinum electrode
Test solution: 0.05 M phosphate
Temperature: 25 ± 0.1°C.

| Example | Monomer | mV/pH | pH range where Nernstian is satisfied |
|---|---|---|---|
| 8 | 3,5-Dimethyl phenol | 59 | 2.3–9.5 |

TABLE 3-continued

Nernstian response of electrode coated with
polymer films of hydroxy aromatic compounds Platinum electrode
Test solution: 0.05 M phosphate
Temperature: 25 ± 0.1°C.

| Example | Monomer | mV/pH | pH range where Nernstian is satisfied |
|---|---|---|---|
| 9 | 2,6-Dimethyl phenol | 59 | 3.5–9.0 |
| 10 | 2-Hydroxypyridine | 59 | 3.5–9.5 |
| 11 | 3-Hydroxypyridine | 59 | 3.5–9.5 |
| 12 | 4-Hydroxypyridine | 59 | 3.5–9.5 |
| 13 | o-Hydroxybenzyl alcohol | 59 | 4.5–9.0 |
| 14 | o-Hydroxybenzaldehyde | 59 | 4.5–7.0 |
| 15 | o-Hydroxyacetophenone | 59 | 5.5–9.0 |
| 16 | m-Hydroxyacetophenone | 59 | 4.4–7.5 |
| 17 | o-Carboxyphenol (Salicylic acid) | 59 | 4.6–9.0 |
| 18 | o-Hydroxypropiophenone | 59 | 2.8–9.1 |
| 19 | p-Hydroxypropiophenone | 59 | 4.5–8.5 |
| 20 | Benzophenol | 59 | 4.7–8.0 |
| 21 | o-Hydroxybenzophenone | 59 | 4.0–11.4 |
| 22 | Salicylanilide | 55 | 6.0–10.5 |
| 23 | 2-Methyl-8-hydroquinone | 59 | 4.5–9.0 |
| 24 | 5-Hydroxy-1,4-naphthoquinone | 55 | 4.5–9.0 |
| 25 | 5-Hydroxyquinoline | 59 | 2.5–10.0 |
| 26 | 8-Hydroxyquinoline | 59 | 2.5–10.5 |
| 27 | 1,8-Dihydroxyanthraquinone | 55 | 6.0–10.5 |

EXAMPLE 28

Phosphate buffer solutions of varying total phosphoric acid content in the range of 0.1M to $5 \times 10^{-4}$M were prepared as test solutions. In a given test solution, the electrode prepared in Example 7 was used for the measurement of electromotive response to the hydrogen ion concentration. A straight line of a slope of 59 mV/pH in the pH range of 3.0 to 10.0 was obtained. This indicates that the electrode can be effectively used as a pH sensor even when a test solution scarcely contains any supporting electrolyte.

EXAMPLE 29

Polyphenylene oxide, poly-2,6-dimethylphenylene oxide and polycarbonate were each dissolved with a concentration of 0.01 weight percent in benzene. The disk surface of the platinum electrode was immersed in the solutions. After several seconds' immersion, the electrode was removed from the solution and then dried, to provide a pH sensor having the same function as the sensor of Example 7. The relation between the electromotive forces and the pH values gave a straight line having a slope of 54 mV/pH for polycarbonate coating. The slope of the other polymer coated electrode was 59 mV/pH.

EXAMPLE 30

A gel-like test solution was used for pH measurement.

The solution contained 5 weight percent of sodium hydroxide and 0.1 weight percent of Carbopol #40 (adhesive material based on polyacrylic acid, Coodrich Co.). When the polymer coated electrode prepared by the procedure of Example 1 was used to measure the pH value of the test solution mentioned above, the equilibrium potential (electromotive force) of the electrode was found to be about 140 mV vs. SSCE. From the graph of FIG. 4 illustrating the relation between the electromotive forces and the pH values, this value of equilibrium potential was found to correspond to a pH value of about 10.5.

When this measurement was repeated by use of a glass electrode, the measurement of the pH value was infeasible because there was no response of equilibrium potential.

EXAMPLE 31

A solution scarcely containing any electrolyte was used for pH measurement.

A known volume of rain water was used as the test solution. A platinum electrode was immersed in this test solution and used as a working electrode for electrolysis. The concentration of hydrogen ions in the test solution was adjusted by suitably performing the electrolysis of water. The amount of electricity consumed for the electrolysis was read out by means of a coulometer. In this case, the total hydrogen in concentration of the test solution could be represented by $$\left( H_o + \frac{Q}{F} \cdot \frac{1}{V_T} \right).$$

In the formula, $H_o$ denotes the analytical excess hydrogen ion concentration contained from the beginning in the test solution, Q the amount of electricity used in the electrolysis, F the Faraday constant, and $V_T$ the volume of the test solution. If the Nernst equation can be applied to the measurement of the electromotive force (E), the following equation is satisfied at 25° C., $$E = E_o + 0.059 \log \left( H_o + \frac{Q}{F} \cdot \frac{1}{V_T} \right)$$

thus, $$10^{\frac{E}{0.059}} = \frac{Q}{V_T \times F} \times 10^{\frac{E_o}{0.059}} + H_o \times 10^{\frac{E_o}{0.059}}$$

The equilibrium potential was measured by using the coated electrode prepared by the electrochemical oxidation polymerization of phenol. When the term $10^{E/0.059}$ was plotted against Q as the variable, a linear relation was obtained. Consequently, the values of $E_o$ and $H_o$ can be determined. Based on the values thus determined, the pH value of the rain water was found to be 5.0.

EXAMPLE 32

The electrochemical oxidation polymerization of 4,4'-diaminodipheny ether was conducted in a methanol solution containing 10 mM of 4,4'-diaminodiphenyl ether and 30 mM of sodium hydroxide. In this case, the electrolytic solution for surface coating of a platinum electrode is different from the solution of Example 1. A stable polymer film of a golden color on the electrode was obtained. The film-coated electrode gave good response as a pH sensor.

EXAMPLE 33

Figure 7:
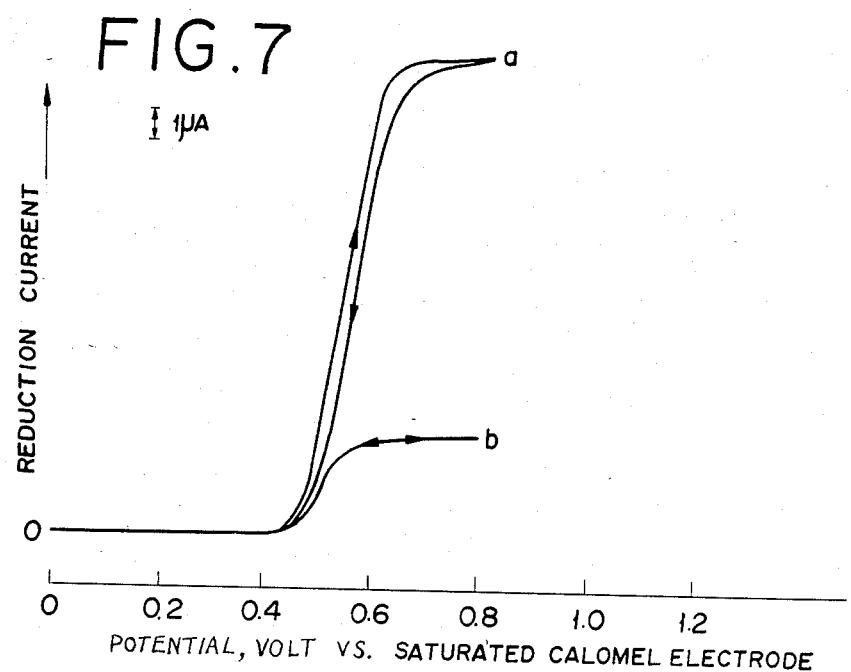
FIGS. 7 and 8 are voltammograms obtained by means of rotating disk electrodes.

The selective permeability of the film coated on the electrode surfaces is demonstrated for several oxidation-reduction species in solution. The function of the film to prevent the electrode surfaces from directly contacting with dissolved ions will also be demonstrated. The test was performed by the hydrodynamic voltammetry method using a rotating disk electrode. First, phenol was chosen as a representative compound of the phenol derivatives. The coating of an electrochemical oxidation polymer film of phenol on the rotating disk platinum electrode was performed in methanol solution containing 10 mM of phenol and 30 mM of sodium hydroxide. Prior to electrolysis, the solution was thoroughly deoxygenated with argon gas. At the applied potential of 1.0 volt vs. SSCE, the electrolysis was performed for three minutes to coat the oxidation polymerization product [poly(phenylene oxide)] on the electrode surfaces. In an aqueous solution of pH 3.00 containing 0.2M $CF_3COONa$ as a supporting electrolyte, the reduction wave of hydrogen ion was observed at a rotating disk electrode coated with the film at a rotation rate 4918 rpm and a potential sweep rate 5 mV/second. The limiting current (curve "b" in FIG. 7) for the reduction wave of hydrogen ion was remarkably smaller than the limiting current obtained with a platinum electrode having no film coating (10 percent of curve "a" in the diagram of FIG. 7). From this fact, it is noted that the coating film permitted passage of a definite amount of hydrogen ion.

Figure 8:
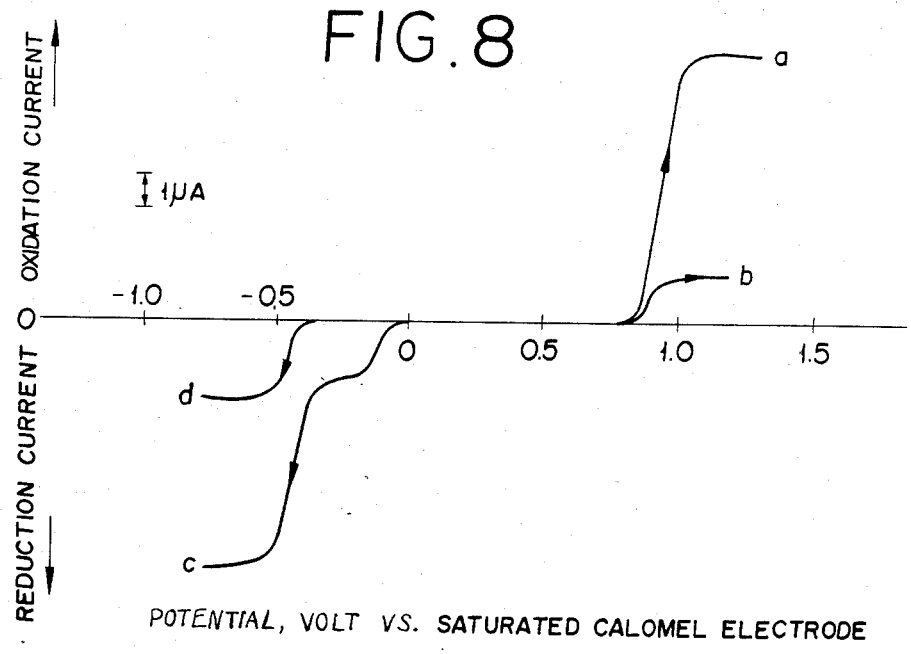

FIG. 8 represents voltammograms obtained with respect to the reduction (curves "c" and "d") of the ethyelnediamine tetraacetate complex of iron (III) ($Fe^{III}(EDTA)$) and the oxidation (curves "a" and "b") of bromide ion ($Br^-$) at rotation rate 932 rpm. It is noted from the limiting current for the various ions that the coating film did not pass $Fe^{III}(EDTA)^-$ but permitted passage of a definite amount of $Br^-$. The reduction wave of $Fe^{III}(EDTA)^-$ was observed in the solution containing 2 mM of $Fe^{III}(EDTA)^-$ and 0.2M of $CF_3COONa$ (pH 3.0), while the oxidation of bromide ion was observed in the solution containing 2.0 mM or $Br^-$ and 0.2M of $CF_3COONa$ (pH 3.0). The curves "a" and "c" represent the data obtained from the electrodes having no film coating thereon and the curves "b" and "d" represent those obtained from the electrodes having the electrochemical oxidation polymer film of phenol.

EXAMPLES 34, 35 and 36

The examples summarized in Table 4 below, demonstrate that polymer films coated on electrodes exhibited selective permeability to ions in solutions.

On the disk platinum electrode, various monomers indicated in Table 4 were polymerized by electrochemical oxidation, to prepare the electrode surfaces directly coated with the corresponding polymer films. The electrochemical oxidation polymerization of phenol was carried out by following the procedure of Example 33 (solvent: methanol), that of aniline by following the procedure of Example 2 (solvent: acetonitrile), and that of 4,4-diaminodiphenyl ether by following the procedure of Example 3 (solvent: acetonitrile).

The three kinds of polymer film-coated electrodes were tested on various dissolved oxidation-reduction species to determine the permeability of the polymer films to ions by the measurement of hydrodynamic voltammetry. As already described in Example 33, it was elucidated that the poly(phenylene oxide) film permitted partial passage of relatively small ions such as hydrogen ion and bromine ion and inhibited passage of the $Fe^{III}(EDTA)^-$ complex.

Figure 9:
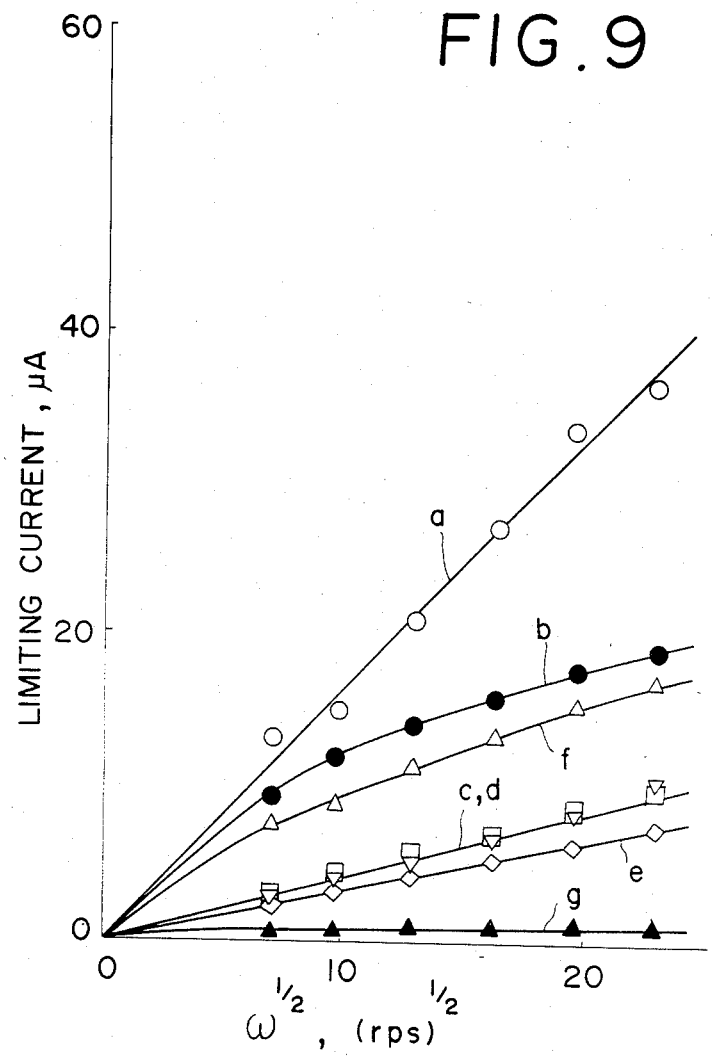
FIG. 9 is a graph showing the limiting current vs. the square root of the rotation rate for the oxidation and the reduction of various species at a rotating disk electrode.

Current-potential curves showing similar ion-permeability were obtained by the electrodes coated with a poly(aniline) film. Iron aqua-ion penetrated the polymer film less easily than hydrogen ion and bromide ion. Relatively large metal complex species such as $Ru(EDTA)^{-1/-2}$, $FE(EDTA)^{-1/-2}$ and $Fe(CN)_6^{-3/-4}$ could not penetrate the poly(phenylene oxide) film and the poly(aniline) film. Their oxidation reduction waves could not be observed. Unlike the poly(phenylene oxide) and poly(aniline) films, the poly(4,4'-diaminodiphenyl ether) film impeded passage of iron (II) aqua ion, in analogy with $Fe(CN)_6^{-3/-4}$, $Fe(EDTA)^{-1/-2}$ and $Ru(EDTA)^{-1/-2}$ species. No oxidation waves could be observed. Plotting the limiting current ($i_{Lim}$) of the hydrodynamic voltammograms against the square root of rotation rate ($\sqrt{\omega}$) is shown in FIG. 9. The lines "a", "c", "d", "e" and "f" in FIG. 9 represent the data obtained with bare platinum disk electrodes and the lines "b" and "g" those obtained with platinum electrodes coated with polymer films. The test solution at 25° C. contained 0.2M of $CF_3COONa$ as a supporting electrolyte and were de-aerated by the bubbling of argon gas. The lines "a" and "b" represent the data obtained by the reaction of $2H^+ + 2e^- \rightarrow H_2$ at a pH value of 3.05, the line "c" that obtained by the reaction of $Fe(EDTA)^{-1} + e^- \rightarrow Fe(EDTA)^{2-}$ (2.0 mM of NaFe(EDTA)), the line "d" that obtained by the reaction of $Fe(CN)_6^{3-} + e^- \rightarrow Fe(CN)_6^{4-}$ (2.0 mM $K_3Fe(CN)_6$), the line "e" that obtained by the reaction of $Fe^{2+} \rightarrow Fe^{3+} + e^-$ (2.0 mM $FeSO_4$) and the lines "f" and "g" those obtained by the reaction of $2Br^- \rightarrow Br_2 + 2e^-$ (2.0 mM NaBr) at pH=3.0. The pH value was adjusted by $CF_3COOH$.

As already described, when the electrode coated with a poly(phenylene oxide) film or a poly(aniline) film was used as a pH sensor, transition metal ions contained in the test solution influenced the equilibrium potential of hydrogen ion. This is because such transition metal ions partially penetrated the coated film as already described.

When the electrode coated with the poly(4,4'-diaminodiphenyl ether) film was used as a pH sensor, transition metal ions gave no observable influences upon the equilibrium potential. It can be understood by the fact that the transition metal ions were incapable of penetrating the poly(4,4'-diaminodiphenyl ether) film, as described above. Thus, the equilibrium potential responded to only the hydrogen ion in the solution.

TABLE 4

| | | Dissolved oxidation-reduction species | | | | |
| --- | --- | --- | --- | --- | --- | --- |
| Example | Monomer | Hydrogen ion | Bromide ion | $Fe^{2+}$ aqua-ion | $Fe(EDTA)^-$ | $Fe(CN)_6^{3-}$ |
| 34 | phenol | Partial permeation | partial permeation | partial permeation | No permeation | No permeation |
| 35 | Aniline | Same as above | Same as above | Same as above | Same as above | Same as above |
| 36 | 4,4'-Diaminodiphenyl ether | Same as above | Same as above | No permeation | Same as above | Same as above |

The test solutions contained 0.2 M of $CF_3COONa$ as a supporting electrolyte.
The oxidation-reduction species were used in concentration of 0.2 mM to 4 mM. The pH value was adjusted by using $CF_3COOH$.
The test solution containing $Fe^{2+}$ aqua-ion was adjusted to pH 1.5.

Then, a stream of hydrogen gas was bubbled into the test solution and the equilibrium potential of the polymer film-coated electrode was measured. The values of equilibrium potentials satisfied a linear relation having the slope of 59 mv/pH. It is believed that the relation satisfying the Nernstian was established between the equilibrium potential and the pH value because the reaction of $2H^+ + 2e^- \rightleftarrows H_2$ generally proceeds reversibly on the platinum electrode. The fact that the electrode coated with the electrochemical oxidation polymer film heretofore regarded as an insulating substance exhibits such a response characteristic as described above will be understood by the assumption that a distribution equilibrium relative to hydrogen ion is established between the polymer coating film and the solution. In this case, the equilibrium potential (E) can be represented by the following equation:

$$E = E^\circ + 59.16 \log K \cdot C^O_{H+}$$

(wherein, K denotes the distribution equilibrium constant of hydrogen ion existing between the solution and the polymer coating film, E° a constant, and $C^O_{H+}$ the hydrogen ion concentration in the solution). This equation is transformed $$10^{\frac{E-E^o}{59.16}} = KC_H^O +.$$

When the term $$10^{\frac{E-E^o}{59.16}}$$

which was calculated from the values of the equilibrium potential measured by the electrode coated with a poly(phenylene oxide) film is plotted relative to the term $C_H^O+$, a linear relation passing the origin was obtained. From the slope of the straight line, the value of K was found to be 0.75.

From the results described above, the following conclusion may be drawn. With the bare platinum electrode which is not coated with any polymer film, the equilibrium potential response to the change of the hydrogen ion in the test solution does not satisfy the Nernstian because of the influence such as of the oxiation film on the bare platinum surface. The equilibrium potential response becomes complicated when transition metal ions or the adsorption species are contained in the test solution. In the case of the platinum electrode coated with an electrochemically polymerized film, particularly a poly(4,4'-diaminodiphenyl ether) film, the equilibrium potential gives a response satisfying the Nernst equation to the hydrogen ion concentration in the test solution through the distribution equilibrium of hydrogen ion between the film and the bulk solution, even when the test solutions contains transition metal ions. The film coated on the electrode prevents the surface of the electrode from directly contacting with dissolved ions and thus the equilibrium potential is not influenced by the metal ions. Thus, the selective passage of hydrogen ion is performed and a stable response is obtained. Further, the film which adheres to the electrode surface seems to contribute to the homogeneity of the surface species of platinum.

The selectively permeable film and the ion sensor according to this invention which has been described above manifest the various effects enumerated below.

(1) The pH value of the test solution is measured with the equilibrium potential response of the electrode coated directly with a polymer film which is derived from a nitrogen-containing aromatic compound or a hydroxy aromatic compound. It, therefore, obviates the necessity for providing itself with a room holding a reference solution, permits its size to be reduced to the limit of its own fabrication, allows of the pH measurement of the high temperature test solution, and requires only a small amount of test solution to perform the measurement. It gives potential response at high speed. The pH sensor of this invention can be fabricated so as to be inserted into the human system.

(2) The polymer film offers very low film resistance and shows low impedance. A voltmeter having high input impedance, therefore, is not required for the purpose of the pH measurement.

(3) Even in a test solution containing different kinds of ions, particularly transition metal ions, the pH measurement can be performed quantitatively and accurately in a short time. The function of a pH sensor is fully manifested even in a test solution of the form of suspension or slurry which contain a heterogeneous substance.

(4) The linear relation satisfying the Nernst equation is established even when oxygen gas, argon gas, or hydrogen gas is bubbled into the test solution. Thus, pH measurement of the test solution can be done under the gas flowing.

(5) The film coated on the surface of the electroconductive element is capable of permitting partial passage of hydrogen ion and bromide ion, providing specifically selective passage of hydrogen ion, and impeding passage of transition metal ions and their complexes. It can be utilized, therefore, as a film for selective passage of ions and molecules.

(6) Since the polymer film shows low impedance, it functions efficiently as a pH sensor even in a test solution such as rain water which has low electroconductivity.

(7) The electrode coated with polymer film of phenol derivatives satisfies the Nernstian response until the alkaline pH-range is more than the respose of glass electrode.

What is claimed is:

1. A system for measuring the concentration of hydrogen ions in a test solution by electrode potential response or current response, comprising:

a hydrogen ion sensor adapted to contact said test solution; and means coupled to said hydrogen ion sensor for measuring the electrical potential difference between said hydrogen ion sensor while contacting said test solution and a reference potential;

said hydrogen ion sensor consisting essentially of an electroconductive element having applied to a surface thereof a polymer film derived from at least one aromatic compound selected from the group consisting of nitrogen-containing aromatic compounds selected from the group consisting of aniline, 2-aminobenzotrifluoride, 2-aminopyridine, 2,3-diaminopyridine, 4,4'-diaminodiphenyl ether, 4,4'-methylenedianiline, tyramine, N-(o-hydroxybenzyl)aniline, and pyrrole and a hydroxy aromatic compound selected from compounds having the formula

wherein Ar is an aromatic ring, R is selected from the group consisting of alkyl, aryl, alkylcarbonyl, arylcarbonyl hydroxyalkyl, carboxyl, aldehyde, and hydroxyl, and l is zero or the valency number of the Ar group.

2. The system of claim 1, wherein the polymer film is a film polymerized by electrochemical oxidation on the surface of the electroconductive element.

3. The system of claim 1, wherein the polymer film is a film obtained by applying to the surface of the electroconductive element a solution of the synthesized polymer.

4. The system of claim 1, wherein the polymer film is derived from said nitrogen-containing aromatic compound.

5. The system of claim 1, wherein said hydrogen ion sensor is a pH sensor.

6. The system of claim 1, wherein the polymer film is derived from said hydroxy aromatic compound.

7. The system of claim 1, wherein the hydroxy aromatic compound is at least one member selected from the group consisting of phenol, dimethyl phenol, hydroxypyridine, o- and m-benzyl alcohols, o-, m- and p-hydroxybenzaldehydes, o-, m- and p-hydroxyacetophenones, o-, m- and p-hydroxypropiophenones, o-, m- and p-benzophenols, o-, m- and p-hydroxybenzophenones, o-, m- and p-carboxyphenols, diphenyl phenol, 2-methyl-8-hydroquinoline, 5-hydroxy-1,4-naphthoquinone, 4-(p-hydroxyphenyl)-2-butanone, 1,5-dihydroxy-1,2,3,4-tetrahydronaphthalene and bisphenol A.

8. A system for measuring the concentration of hydrogen ions in a test solution by electrode potential response or current response, comprising:

a hydrogen ion sensor adapted to contact said test solution; and means coupled to said hydrogen ion sensor for measuring the electrical potential difference between said hydrogen ion sensor while contacting said test solution and a reference potential;

said hydrogen ion sensor comprising an electroconductive element having applied to a surface thereof a polymer film derived from at least one aromatic compound selected from the group consisting of nitrogen-containing aromatic compounds selected from the group consisting of aniline, 2-aminobenzotrifluoride, 2-aminopyridine, 2,3-diaminopyridine, 4,4'-diaminodiphenyl ether, 4,4'-methylenedianiline tyramine, N-(o-hydroxybenzyl)aniline, and pyrrole.

* * * * *